United States Patent
Helkowski et al.

(10) Patent No.: US 10,045,881 B2
(45) Date of Patent: Aug. 14, 2018

(54) PATIENT TEMPERATURE CONTROL CATHETER WITH HELICAL HEAT EXCHANGE PATHS

(75) Inventors: Richard A. Helkowski, Redwood City, CA (US); Jeremy T. Dabrowiak, Redwood City, CA (US); Venkata Vishnu Gurukula, Mountain View, CA (US); Alex L. Lim, Santa Clara, CA (US)

(73) Assignee: Zoll Circulation, Inc., San Jose, CA (US)

( * ) Notice: Subject to any disclaimer, the term of this patent is extended or adjusted under 35 U.S.C. 154(b) by 1147 days.

(21) Appl. No.: 13/247,073

(22) Filed: Sep. 28, 2011

(65) Prior Publication Data

US 2013/0079855 A1     Mar. 28, 2013

(51) Int. Cl.
*A61F 7/12*     (2006.01)
*A61B 17/00*    (2006.01)

(52) U.S. Cl.
CPC ...... *A61F 7/12* (2013.01); *A61B 2017/00867* (2013.01); *A61F 2007/126* (2013.01)

(58) Field of Classification Search
USPC ................................................. 607/105–106
See application file for complete search history.

(56) References Cited

U.S. PATENT DOCUMENTS

| | | |
|---|---|---|
| 1,459,112 A | 6/1923 | Mehl |
| 1,857,031 A | 5/1932 | Schaffer |
| 2,663,030 A | 12/1953 | Dahlberg |
| 2,673,987 A | 4/1954 | Upshaw et al. |
| 3,225,191 A | 12/1965 | Calhoun |
| 3,369,549 A | 2/1968 | Armao |
| 3,425,419 A | 2/1969 | Dato |
| 3,504,674 A | 4/1970 | Swenson |
| 3,726,269 A | 4/1973 | Webster, Jr. |
| 3,744,555 A | 7/1973 | Fletcher et al. |
| 3,751,077 A | 8/1973 | Hiszpanski |
| 3,937,224 A | 2/1976 | Uecker |
| 3,945,063 A | 3/1976 | Matsuura |
| 4,038,519 A | 7/1977 | Foucras |
| 4,065,264 A | 12/1977 | Lewin |
| 4,103,511 A | 8/1978 | Kress et al. |
| 4,126,132 A | 11/1978 | Fortner et al. |
| 4,153,048 A | 5/1979 | Magrini |
| 4,173,228 A | 11/1979 | Van Steenwyk et al. |

(Continued)

FOREIGN PATENT DOCUMENTS

| | | |
|---|---|---|
| DE | 19531935 | 2/1997 |
| GB | 2040169 | 8/1980 |

(Continued)

OTHER PUBLICATIONS

F.W. Behmann, E. Bontke, "Die Regelung der Wärmebildung bei künstlicher Hypothermie", Pflügers Archiv, Bd. 266, S. 408-421 (1958).

(Continued)

*Primary Examiner* — Joseph Stoklosa
*Assistant Examiner* — Adam Avigan
(74) *Attorney, Agent, or Firm* — John L. Rogitz

(57) ABSTRACT

A catheter includes a working fluid supply path communicating with a source of working fluid. The catheter also includes a working fluid return path communicating with the working fluid supply path to return working fluid from the supply path to the source of working fluid. At least one of the paths is contained in a distal heat exchange region of the catheter, where the distal heat exchange region includes first and second helical paths and is made of a shape memory material.

8 Claims, 2 Drawing Sheets

(56) References Cited

U.S. PATENT DOCUMENTS

| | | |
|---|---|---|
| 4,181,132 A | 1/1980 | Parks |
| 4,298,006 A | 11/1981 | Parks |
| 4,459,468 A | 7/1984 | Bailey |
| 4,532,414 A | 7/1985 | Shah et al. |
| 4,554,793 A | 11/1985 | Harding, Jr. |
| 4,581,017 A | 4/1986 | Sahota |
| 4,638,436 A | 1/1987 | Badger et al. |
| 4,653,987 A | 3/1987 | Tsuji et al. |
| 4,661,094 A | 4/1987 | Simpson |
| 4,665,391 A | 5/1987 | Spani |
| 4,672,962 A | 6/1987 | Hershenson |
| 4,754,752 A | 7/1988 | Ginsburg et al. |
| 4,787,388 A | 11/1988 | Hofmann |
| 4,813,855 A | 3/1989 | Leveen et al. |
| 4,849,196 A | 7/1989 | Yamada et al. |
| 4,852,567 A | 8/1989 | Sinofsky |
| 4,860,744 A | 8/1989 | Johnson et al. |
| 4,906,237 A | 3/1990 | Johansson et al. |
| 4,941,475 A | 7/1990 | Williams et al. |
| 5,092,841 A | 3/1992 | Spears |
| 5,103,360 A | 4/1992 | Maeda |
| 5,106,360 A | 4/1992 | Ishiwara et al. |
| 5,192,274 A | 3/1993 | Bierman |
| 5,195,965 A | 3/1993 | Shantha |
| 5,211,631 A | 5/1993 | Sheaff |
| 5,269,758 A | 12/1993 | Taheri |
| 5,281,215 A | 1/1994 | Milder |
| 5,304,214 A | 4/1994 | DeFord et al. |
| 5,334,346 A | 8/1994 | Kim et al. |
| 5,342,301 A | 8/1994 | Saab |
| 5,344,436 A | 9/1994 | Fontenot et al. |
| 5,370,675 A | 12/1994 | Edwards et al. |
| 5,383,856 A | 1/1995 | Bersin |
| 5,403,281 A | 4/1995 | O'Neill et al. |
| 5,433,740 A | 7/1995 | Yamaguchi |
| 5,437,673 A | 8/1995 | Baust et al. |
| 5,458,639 A | 10/1995 | Tsukashima et al. |
| 5,466,208 A | 11/1995 | Jackson et al. |
| 5,486,207 A | 1/1996 | Mahawili |
| 5,507,792 A | 4/1996 | Mason et al. |
| 5,531,714 A | 7/1996 | Dahn et al. |
| 5,531,776 A | 7/1996 | Ward et al. |
| 5,542,928 A | 8/1996 | Evans et al. |
| 5,624,392 A | 4/1997 | Saab |
| 5,634,907 A | 6/1997 | Rani et al. |
| 5,676,670 A | 10/1997 | Kim |
| 5,701,905 A | 12/1997 | Esch |
| 5,709,564 A | 1/1998 | Yamada et al. |
| 5,709,654 A | 1/1998 | Klatz et al. |
| 5,716,386 A | 2/1998 | Ward et al. |
| 5,730,720 A | 3/1998 | Sites et al. |
| 5,733,319 A | 3/1998 | Neilson et al. |
| 5,737,782 A | 4/1998 | Matsuura et al. |
| 5,776,079 A | 7/1998 | Cope et al. |
| 5,788,647 A | 8/1998 | Eggers |
| 5,837,003 A | 11/1998 | Ginsburg |
| 5,862,675 A | 1/1999 | Scaringe et al. |
| 5,895,418 A | 4/1999 | Saringer |
| 5,908,407 A | 6/1999 | Frazee et al. |
| 5,957,963 A | 9/1999 | Dobak, III |
| 5,980,561 A | 11/1999 | Kolen et al. |
| 6,019,783 A | 2/2000 | Philips et al. |
| 6,042,559 A | 3/2000 | Dobak, III |
| 6,051,019 A | 4/2000 | Dobak, III |
| 6,059,825 A | 5/2000 | Hobbs et al. |
| 6,096,068 A | 8/2000 | Dobak, III et al. |
| 6,106,518 A | 8/2000 | Wittenberger et al. |
| 6,110,139 A | 8/2000 | Loubser |
| 6,117,065 A | 9/2000 | Hastings et al. |
| 6,117,105 A | 9/2000 | Bresnaham et al. |
| 6,124,452 A | 9/2000 | Di Magno |
| 6,126,684 A | 10/2000 | Gobin et al. |
| 6,146,141 A | 11/2000 | Schumann |
| 6,146,411 A | 11/2000 | Noda et al. |
| 6,148,634 A | 11/2000 | Sherwood |
| 6,149,670 A | 11/2000 | Worthen et al. |
| 6,149,677 A | 11/2000 | Dobak, III |
| 6,231,594 B1 | 5/2001 | Dae |
| 6,283,940 B1 | 9/2001 | Mulholland |
| 6,299,599 B1 | 10/2001 | Pham et al. |
| 6,338,727 B1 | 1/2002 | Noda et al. |
| 6,383,144 B1 | 5/2002 | Mooney et al. |
| 6,409,747 B1 | 6/2002 | Gobin et al. |
| 6,416,533 B1 | 7/2002 | Gobin et al. |
| 6,428,563 B1 | 8/2002 | Keller |
| 6,450,990 B1 | 9/2002 | Walker et al. |
| 6,451,045 B1 * | 9/2002 | Walker ............... A61F 7/12 607/104 |
| 6,464,716 B1 | 10/2002 | Dobak, III et al. |
| 6,527,798 B2 | 3/2003 | Ginsburg et al. |
| 6,530,946 B1 | 3/2003 | Noda et al. |
| 6,540,771 B2 * | 4/2003 | Dobak et al. ............... 607/105 |
| 6,544,282 B1 | 4/2003 | Dae et al. |
| 6,551,309 B1 | 4/2003 | Le Pivert |
| 6,554,791 B1 | 4/2003 | Cartledge et al. |
| 6,605,106 B2 | 8/2003 | Schwartz |
| 6,610,083 B2 | 8/2003 | Keller et al. |
| 6,620,187 B2 | 9/2003 | Carson et al. |
| 6,620,188 B1 | 9/2003 | Ginsburg et al. |
| 6,624,679 B2 | 9/2003 | Tomaivolo et al. |
| 6,635,079 B2 | 10/2003 | Ginsburg |
| 6,679,906 B2 | 1/2004 | Hammack et al. |
| 6,685,733 B1 | 2/2004 | Dae et al. |
| 6,706,060 B2 | 3/2004 | Tzeng et al. |
| 6,716,188 B2 | 4/2004 | Noda et al. |
| 6,719,723 B2 | 4/2004 | Werneth |
| 6,719,779 B2 | 4/2004 | Daoud |
| 6,726,653 B2 | 4/2004 | Noda et al. |
| 6,740,109 B2 | 5/2004 | Dobak, III |
| 6,799,342 B1 | 10/2004 | Jarmon |
| 6,843,800 B1 | 1/2005 | Dobak, III |
| 6,887,263 B2 | 5/2005 | Bleam et al. |
| 6,893,419 B2 | 5/2005 | Noda et al. |
| 6,969,399 B2 | 11/2005 | Schock et al. |
| 7,255,709 B2 * | 8/2007 | Walker et al. ............... 607/105 |
| 7,371,254 B2 * | 5/2008 | Dobak, III ............... 607/104 |
| 7,510,569 B2 | 3/2009 | Dae et al. |
| 7,666,215 B2 | 3/2010 | Callister et al. |
| 7,822,485 B2 | 10/2010 | Collins |
| 7,846,193 B2 | 12/2010 | Dae et al. |
| 7,857,781 B2 | 12/2010 | Noda et al. |
| 8,105,262 B2 | 1/2012 | Noda et al. |
| 8,105,263 B2 | 1/2012 | Noda et al. |
| 8,105,264 B2 | 1/2012 | Noda et al. |
| 8,109,894 B2 | 2/2012 | Noda et al. |
| 2001/0001832 A1 | 5/2001 | Dobak, III |
| 2001/0007951 A1 | 7/2001 | Dobak, III |
| 2001/0031946 A1 | 10/2001 | Walker et al. |
| 2001/0032003 A1 | 10/2001 | Pecor |
| 2001/0047196 A1 | 11/2001 | Ginsburg et al. |
| 2002/0013569 A1 | 1/2002 | Sterman et al. |
| 2002/0022823 A1 | 2/2002 | Luo et al. |
| 2002/0116039 A1 | 8/2002 | Walker et al. |
| 2002/0145525 A1 | 10/2002 | Friedman et al. |
| 2002/0151942 A1 | 10/2002 | Walker et al. |
| 2002/0183692 A1 | 12/2002 | Callister |
| 2002/0198578 A1 * | 12/2002 | Dobak, III ............... 607/104 |
| 2002/0198579 A1 | 12/2002 | Khanna |
| 2003/0088240 A1 | 5/2003 | Saadat |
| 2003/0036496 A1 | 12/2003 | Samson et al. |
| 2004/0089058 A1 | 5/2004 | De Hann et al. |
| 2004/0102825 A1 | 5/2004 | Daoud |
| 2004/0210231 A1 | 10/2004 | Boucher et al. |
| 2005/0156744 A1 | 7/2005 | Pires |
| 2007/0007640 A1 | 1/2007 | Harnden et al. |
| 2007/0076401 A1 | 4/2007 | Carrez et al. |
| 2010/0057063 A1 | 4/2010 | Arless et al. |

FOREIGN PATENT DOCUMENTS

| | | |
|---|---|---|
| GB | 1183185 | 2/1985 |
| GB | 2212262 | 7/1989 |
| GB | 2383828 | 7/2003 |

(56) References Cited

FOREIGN PATENT DOCUMENTS

| | | |
|---|---|---|
| JP | 09-215754 | 8/1997 |
| JP | 10-0127777 | 5/1998 |
| JP | 10-305103 | 11/1998 |
| JP | 2002500915 A | 1/2002 |
| WO | 1990001682 | 2/1990 |
| WO | 1993004727 | 3/1993 |
| WO | 1994000177 | 1/1994 |
| WO | 1994001177 | 1/1994 |
| WO | 1997025011 | 7/1997 |
| WO | 1998024491 | 6/1998 |
| WO | 1998040017 | 9/1998 |
| WO | 2000010494 | 3/2000 |
| WO | 2000018327 | 4/2000 |
| WO | 2001013809 | 3/2001 |
| WO | 2001064146 | 9/2001 |
| WO | 2001076517 | 10/2001 |
| WO | 2001083001 | 11/2001 |
| WO | 200207625 | 10/2003 |

OTHER PUBLICATIONS

F.W. Behmann, E. Bontke, "Intravasale Kühlung", Pflügers Archiv, Bd. 263, S. 145-165 (1956).

Wilhelm Behringer, Stephan Prueckner, Rainer Kenter, Samuel A. Tisherman, Ann Radovsky, Robert Clark, S. William Stezoski, Heremy Henchir, Edwin Klein, Peter Safar, "Rapid Hypothermic Aortic Flush Can Achieve Survival without Brain Damage after 30 Minutes Cardiac Arrest in Dogs", anesthesiology, V. 93, No. 6, Dec. 2000.

Dorraine Day Watts, Arthur Trask, Karen Soeken, Philip Predue, Sheilah Dols, Christopher Kaufman; "Hypothermic Coagulopathy in trauma: Effect of Varying levels of Hypothermia on Enzyme Speed, Platelet Function, and Fibrinolytic Activity". The Journal of Trauma: Injury, Infection, and Critical Care, Vo. 44, No. 5 (1998).

Mark A. Saab, "Multi-Lumen Heat Transfer Catheter System", file history of pending U.S. Appl. No. 12/924,933, filed Oct. 8, 2010.

David J. Scott, Ben F. Brian, Lloyd F. Wright, Leo A. Chin, Edward W. Hollmen, Saniel W. Seegars, Mark a. Logan, "Apparatus and Method for Providing Enhanced Heat Transfer from a Body", file history of pending U.S. Appl. No. 12/897,637, filed Oct. 4, 2010.

Timothy R. Machold, Nicole Denise Bloom, Alex T. Roth, Dave J. Scott, Jose Alejandro, Edward A. Oliver, "Method and Apparatus for Regional and Whole Body Temperature Modification", file history of pending U.S. Appl. No. 13/101,000, filed May 4, 2011.

Timothy R. Machold, Nicole Denise Bloom, Alex T. Roth, Dave J. Scott, Jose Alejandro, Edward A. Oliver, "Method and Apparatus for Regional and Whole Body Temperature Modification", file history of pending U.S. Appl. No. 13/101,036, filed May 4, 2011.

Timothy R. Machold, Wade A. Keller, Alex T. Roth, Nicole Denise Bloom, "Method and System for Control of a Patient's Body Temperature by Way of a Transluminally Insertable Heat Exchange Catheter", file history of pending U.S. Appl. No. 13/161,648, filed Jun. 20, 2011.

* cited by examiner

PATIENT TEMPERATURE CONTROL CATHETER WITH HELICAL HEAT EXCHANGE PATHS

I. FIELD OF THE INVENTION

The present application relates generally to patient temperature control systems.

II. BACKGROUND OF THE INVENTION

It has been discovered that the medical outcome for a patient suffering from severe brain trauma or from ischemia caused by stroke or heart attack or cardiac arrest is improved if the patient is cooled below normal body temperature (37° C.). Furthermore, it is also accepted that for such patients, it is important to prevent hyperthermia (fever) even if it is decided not to induce hypothermia. Moreover, in certain applications such as post-CABG surgery, it might be desirable to re-warm a hypothermic patient.

As recognized by the present application, the above-mentioned advantages in regulating temperature can be realized by cooling or heating the patient's entire body using a closed loop heat exchange catheter placed in the patient's venous system and circulating a working fluid such as saline through the catheter, heating or cooling the working fluid as appropriate in an external heat exchanger that is connected to the catheter. The following U.S. patents, all of which are incorporated herein by reference, disclose various intravascular catheters/systems/methods for such purposes: U.S. Pat. Nos. 6,881,551 and 6,585,692 (tri-lobe catheter), U.S. Pat. Nos. 6,551,349 and 6,554,797 (metal catheter with bellows), U.S. Pat. Nos. 6,749,625 and 6,796,995 (catheters with non-straight; non-helical heat exchange elements), U.S. Pat. Nos. 6,126,684, 6,299,599, 6,368,304, and 6,338,727 (catheters with multiple heat exchange balloons), U.S. Pat. Nos. 6,146,411, 6,019,783, 6,581,403, 7,287,398, and 5,837,003 (heat exchange systems for catheter), U.S. Pat. No. 7,857,781 (various heat exchange catheters).

SUMMARY OF THE INVENTION

Accordingly, a catheter includes a working fluid supply path communicating with a source of working fluid and a working fluid return path communicating with the working fluid supply path to return working fluid from the supply path to the source of working fluid. At least one of the supply path and/or return path is contained in a distal heat exchange region of the catheter, where the distal heat exchange region is to be disposed in a patient. The distal heat exchange region includes at least first and second helical paths and may be made of a shape memory material. In non-limiting embodiments, the shape memory material may be nitinol.

Furthermore, the helical paths described herein may overlap each other to establish a double helical structure in non-limiting embodiments, or they may not overlap each other in other non-limiting embodiments. If desired, the first helical, path may be in the working fluid supply path, or both the first and second helical paths may be in the working fluid supply path. Alternatively, the first helical path may be in the working fluid return path in non-limiting embodiments, or the first and second helical paths may be in the working fluid return path in still other non-limiting embodiments.

In another aspect, a method includes providing a working fluid supply path that at least in part defines a catheter and that is in fluid communication with a source of working fluid. The method also includes providing a working fluid return path that at least in part defines the catheter and is in fluid communication with the working fluid supply path to return working fluid from the supply path to the source of working fluid. At least one of the paths provided by the method disclosed herein is contained in a distal heat exchange region of the catheter, where the distal heat exchange region includes first and second helical paths.

In still another aspect, a catheter includes a working fluid supply path communicating with a source of working fluid and a working fluid return path communicating with the working fluid supply path to return working fluid from the supply path to the source of working fluid. At least one of the supply and/or return paths is contained in a heat exchange region of the catheter, where the heat exchange region is to be positioned into a patient. The heat exchange region includes plural helical paths, where the plural helical paths are understood not to be limited to only two helical paths.

The details of the present invention, both as to its structure and operation, can best be understood in reference to the accompanying drawings, in which like reference numerals refer to like parts, and in which:

DETAILED DESCRIPTION OF THE PREFERRED EMBODIMENT

Figure 1:
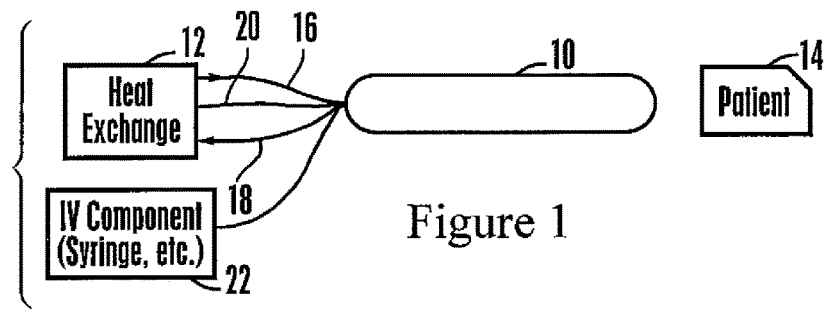
FIG. 1 is a schematic diagram showing an example catheter engaged with an example heat exchange system.

Referring initially to FIG. 1, an intravascular temperature management catheter 10 is in fluid communication with a catheter temperature control system 12 that includes a processor executing logic described in one or more of the patents referenced herein to control the temperature of working fluid circulating through the catheter 10 in accordance with a treatment paradigm responsive to patient core temperature feedback signals. In accordance with present principles, the catheter 10 can be used to induce therapeutic hypothermia in a patient 14 using the catheter, in which coolant such as but not limited to saline circulates in a closed loop, such that no coolant enters the body. Such treatment may be indicated for stroke, cardiac arrest (post-resuscitation), acute myocardial infarction, spinal injury, and traumatic brain injury. The catheter 10 can also be used to warm a patient, e.g., after bypass surgery or burn treatment, and to combat hyperthermia in, e.g., patient suffering from subarachnoid hemorrhage or intracerebral hemorrhage.

As shown, working fluid may be circulated between the heat exchange system 12 and catheter 10 through supply and return lines 16, 18 that connect to the proximal end of the catheter 10 as shown. Note that as used herein, "proximal" and "distal" in reference to the catheter are relative to the system 12. A patient temperature signal from a. catheter-borne temperature sensor may be provided to the system 12 through an electrical line 20 or wirelessly if desired. Alternatively, a patient temperature signal may be provided to the system 12 from a separate esophageal probe or rectal probe or tympanic sensor or bladder probe or other temperature probe that measures the temperature of the patient 14.

The catheter 10, in addition to interior supply and return lumens through which the working fluid is circulated, may also have one or more infusion lumens connectable to an IV component 22 such as a syringe or IV bag for infusing medicaments into the patient, or an instrument such as an oxygen or pressure monitor for monitoring patient parameters, etc.

The catheter 10 can be positioned typically in the vasculature of the patient 14 and more preferably in the venous system of the patient 14 such as in the inferior vena cava through a groin insertion point or the superior vena cava through a neck (jugular or subclavian) insertion point.

Next, regarding FIGS. 2-6, it is to be understood that while certain aspects and/or components of the example catheter described in reference to FIG. 1 have been omitted in FIGS. 2-6 for clarity, those aspects and/or components may still be present in the catheters described in reference to FIGS. 2-6 in non-limiting embodiments. For instance, the IV component, temperature sensor, and electrical line described in reference to FIG. 1 are not shown in FIGS. 2-6, but may still be present.

Figures 2, 3, 4:
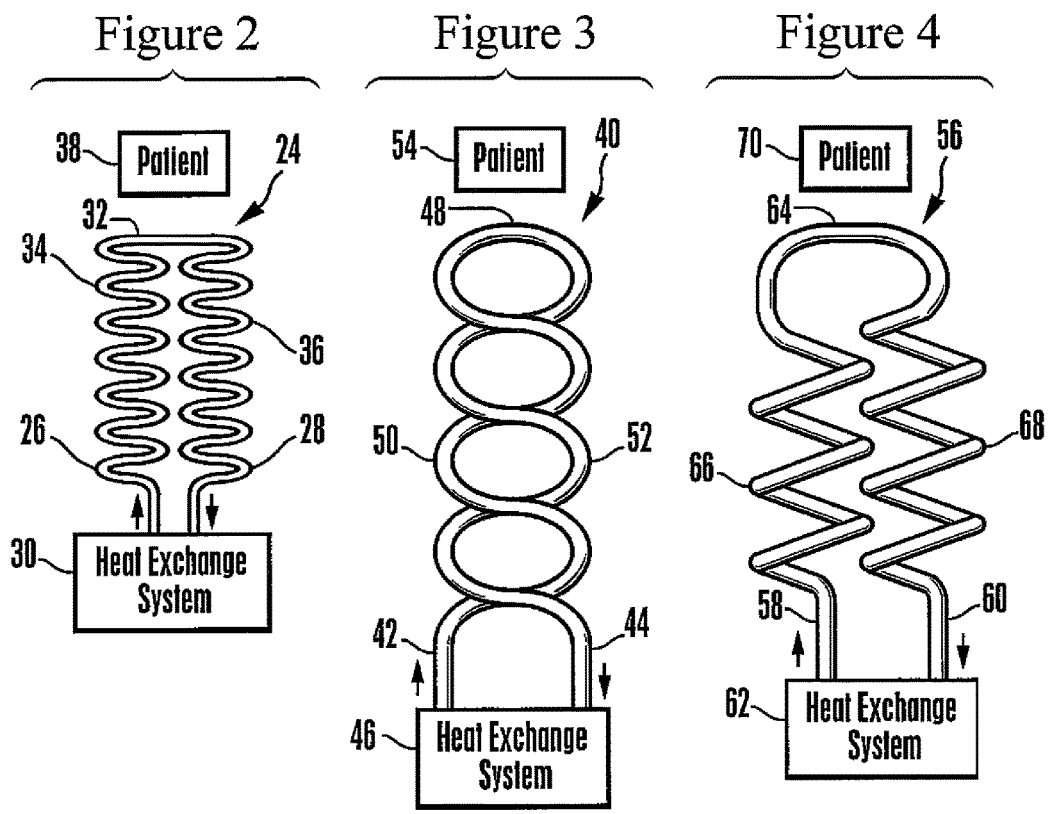
FIG. 2 is a schematic diagram of a catheter having generally cylindrical helical paths that do not overlap each other.
FIG. 3 is a schematic diagram of a catheter having generally cylindrical helical paths that overlap each other to establish a double helical structure.
FIG. 4 is a schematic diagram of a catheter having generally conical helical paths that do not overlap each other.

Now in reference to FIG. 2 specifically, a catheter is shown having generally cylindrical helical paths that do not overlap each other is shown. More specifically, a catheter 24 has a working fluid supply path 26 communicating with a source of working fluid in accordance with present principles, such as the heat exchange system 30 shown in FIG. 2. The catheter 24 also has a working fluid return path 28 in fluid communication with the working fluid supply path 26 to return working fluid from the supply path 26 to the heat exchange system 30.

The catheter 24 also has a distal heat exchange region 32 which may be positioned into a patient, such as the patient 38, wherein at least one of the paths 26 and/or 28 are contained in the distal heat exchange region 32 of the catheter 24. Further, the distal heat exchange region 32 may include a first helical path 34 and a second helical path 36 in fluid communication with each other. In the non-limiting embodiment shown in FIG. 2, the paths 34 and 36, which respectively are the working fluid supply and return paths, substantially comprise the distal heat exchange region 32 such that there is no central, generally linear body extending therethrough along the axis of the catheter 24 as would be the case with a straight tube having its sides formed with a helical or spiral shape. In other words, all of the working fluid flowing through the paths 34, 36 are channeled in helical paths.

In non-limiting embodiments, the distal heat exchange region 32 shown in FIG. 2, as well as the other distal heat exchange regions described in reference to FIGS. 3-6, may be made of a shape memory material such as, but not limited to, nitinol. However, it is to be understood that the heat exchange regions as disclosed herein may still be flexible and/or pliant in non-limiting embodiments such that the catheters of FIGS. 2-6, may be positioned into a patient with ease when, e.g., the catheter enters the patient at an angle relative to the surface area of the portion of the patient in which the catheter is being positioned. Alternatively, in other non-limiting embodiments the heat exchange region 32 may be rigid, if desired.

Still in reference to FIG. 2 and as mentioned above, the first helical path 34 is in and/or defines at least a portion of the supply path 26. Also in non-limiting embodiments, the second helical path 36 is in and/or defines at least a portion of the return path 28. It may now be appreciated from FIG. 2 that the first helical path 34 and second helical path 36 do not overlap each other. Furthermore, while the helical paths 34 and 36 as shown in FIG. 2 are understood to be generally cylindrical, the helical paths 34 and 36 need not be cylindrical and/or symmetrical in accordance with present principles.

Additionally, it is to be understood that, in other non-limiting embodiments, the first and second helical paths of FIG. 2 (as well as the first and second helical paths of FIGS. 3-6, described below) may both be in the working fluid supply path such that an alternate return path returns fluid to the heat exchange system, or may both be in the working fluid return path such that an alternate supply path also not shown supplies fluid from the heat exchange system. It is to be further understood that, in still other non-limiting embodiments, the first helical path of FIGS. 2-6 may be in the working fluid return path and the second helical path of FIGS. 2-6 may be in the working fluid supply path. In other words, multiple non-limiting configurations of the fluid communication between the first and second paths as described herein and the source of working fluid may be provided in accordance with present principles.

In embodiments in which the helical paths are made of shape memory material, they may be deformed into a radially smaller or constricted configuration such as, for example, a straight, non-helical, side-by-side configuration for insertion and withdrawal from the patient. Then, once inside the patient, the paths may be released to assume their enlarged helical shapes for maximizing heat exchange with the blood. Heating may be used to effect this configuration change, or the catheter may simply be advanced into the patient through an introducer sheath that confines the paths and deforms them into sufficiently small configurations to fit inside the sheath, upon the exit of which at the distal end the paths assume the helical shape to which they are biased.

Now in reference to FIG. 3, a catheter having generally cylindrical helical paths that overlap each other to establish a double helical structure is shown. Thus, a catheter 40 has a working fluid supply path 42 communicating with a source of working fluid in accordance with present principles, such as the heat exchange system 46 shown in FIG. 3. The catheter 40 also has a working fluid return path 44 in fluid communication with the working fluid supply path 42 to return working fluid from the supply path 42 to the heat exchange system 46.

The catheter 40 also has a distal heat exchange region 48 which may be positioned into a patient, such as the patient 54, wherein at least one of the paths 42 and/or 44 are contained in the distal heat exchange region 48 of the catheter 40. Furthermore, it is to be understood that the distal heat exchange region 48 may include plural helical paths, though only two helical paths are shown in FIG. 3 for clarity. Accordingly, FIG. 3 shows a first helical path 50 and a second helical path 52 in fluid communication with each other. It is to be understood that while the helical paths 50 and 52 as shown in FIG. 3 are understood to be generally cylindrical, the helical paths 50 and 52 need not be cylindrical and/or symmetrical in accordance with present principles.

In the non-limiting embodiment shown in FIG. 3, the first helical path 50 is in and/or defines at least a portion of the supply path 42. Also in non-limiting embodiments, the second helical path 52 is in and/or defines at least a portion of the return path 44. It may be appreciated from FIG. 3 that the first helical path 50 and second helical path 52 overlap each other to establish a double helical structure along the axis of the catheter 40, where the double helical structure is generally cylindrical. Essentially, the paths 50, 52 are coaxial with each other.

Moving on to FIG. 4, a catheter having generally conical helical paths that do not overlap each is shown. Thus, a catheter 56 has a working fluid supply path 58 communicating with a source of working fluid in accordance with present principles, such as the heat exchange system 62 shown in FIG. 4. The catheter 56 also has a working fluid return path 60 in fluid communication with the working fluid supply path 58 to return working fluid from the supply path 58 to the heat exchange system 62.

The catheter 56 also has a distal heat exchange region 64 in accordance with present principles, which maybe positioned into a patient such as the patient 70. The region 64 includes a first helical path 66 and a second helical path 68 in fluid communication with each other. As shown in FIG. 4, the helical paths 66 and 68 are understood to be generally conical, though the conical helical paths 66 and 68 need not necessarily be symmetrical in accordance with present principles.

Also in accordance with present principles, the first helical path 66 is in and/or defines at least a portion of the supply path 58 in non-limiting embodiments. Also in non-limiting embodiments, the second helical path 68 is in and/or defines at least a portion of the return path 60. As may be appreciated from FIG. 4, the generally conical helical paths 66 and 68 do not overlap each other.

Figure 5:
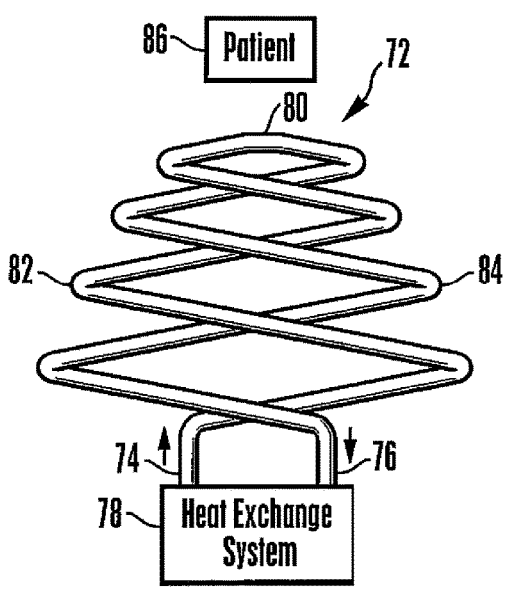
FIG. 5 is a schematic diagram of a catheter having generally conical helical paths that overlap each other to establish a double helical structure.

FIG. 5 also shows a catheter having generally conical helical paths, but in FIG. 5 the generally conical helical paths overlap each other to establish a double helical structure. Thus, a catheter 72 has a working fluid supply path 74 communicating with a source of working fluid in accordance with present principles, such as the heat exchange system 78 shown in FIG. 5. The catheter 72 also has a working fluid return path 76 in fluid communication with the working fluid supply path 74 to return working fluid from the supply path 74 to the heat exchange system 78.

The catheter 72 also has a distal heat exchange region 80 in accordance with present principles, which may be positioned into a patient such as the patient 86. As may be seen in FIG. 5, the region 80 of the catheter 72 includes a first helical path 82 and a second helical path 84 in fluid communication with each other. Further, as shown in FIG. 5, the helical paths 82 and 84 are understood to be generally conical, though the helical paths 82 and 84 need not necessarily be symmetrical in accordance with present principles.

Also in accordance with present principles, the first helical path 82 is in and/or defines at least a portion of the supply path 74 in non-limiting embodiments. Also in non-limiting embodiments, the second helical path 84 is in and/or defines at least a portion of the return path 76. As may be appreciated from FIG. 5, the generally conical helical paths 82 and 84 overlap each other to establish a double helical structure along the axis of the catheter 72.

Figure 6:
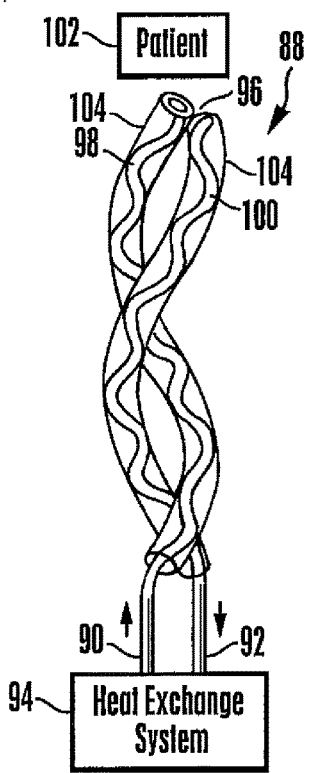
FIG. 6 is a schematic diagram of a catheter having helical paths that establish a generally super-helical structure.

Now in reference to FIG. 6, a catheter having helical paths establishing a generally super-helical structure is shown. Thus, a catheter 88 has a working fluid supply path 90 communicating with a source of working fluid in accordance with present principles, such as the heat exchange system 94 shown in FIG. 6. The catheter 88 also has a working fluid return path 92 in fluid communication with the working fluid supply path 90 to return working fluid from the supply path 90 to the heat exchange system 94.

The catheter 88 also has a distal heat exchange region 96 in accordance with present principles, which may be positioned into a patient such as the patient 102. As may be seen in FIG. 6, the region 96 of the catheter 88 includes a first helical path 98 and a second helical path 100 in fluid communication with each other. As shown in FIG. 6, the helical paths 98 and 100 are understood to be generally conical, though the helical paths 98 and 100 need not necessarily be conical and/or symmetrical in accordance with present principles.

It may be appreciated from FIG. 6 that the helical paths 98 and 100 are coiled to establish a super-helical structure on the distal heat exchange region 96. Note that as understood herein, a superhelix (and the generally super-helical structure shown in FIG. 6) are understood to be plural helices that are coiled into a helix. Further, note that while the paths 98 and 100 are surrounded by respective helical outlines 104 in the schematic diagram shown, the outlines 104 are provided only as a visual aid to demonstrate the super-helical structure established by the paths 98 and 100.

Still in reference to FIG. 6, the first helical path 98 is in and/or defines at least a portion of the supply path 90 in non-limiting embodiments. Also in non-limiting embodiments, the second helical path 100 is in and/or defines at least a portion of the return path 92. Thus, as may now be appreciated from FIG. 6, the helical paths 98 and 100, each having their own respective helical structure, are coiled to establish a generally super-helical structure.

Figure 7:
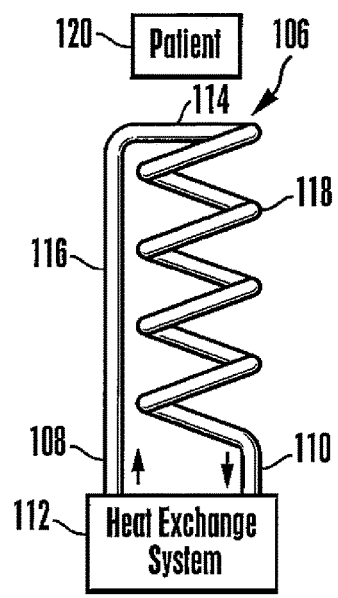
FIG. 7 shows another embodiment of the catheter with a straight supply tube that is parallel to but not coaxial with the axis of a helical return tube, to ensure the coldest coolant is rapidly delivered to the distal-most portion of the catheter.

Moving on to FIG. 7, a catheter having a linear (straight) working fluid supply path and a generally helical working fluid return path is shown. Note that the linear working fluid supply path as described in reference to FIG. 7 is not to be confused with a generally linear body extending through a catheter, as described above. Thus, a catheter 106 has a working fluid supply path 108 communicating with a source of working fluid in accordance with present principles, such as the heat exchange system 112 shown in FIG. 7. The catheter 106 also has a working fluid return path 110 in fluid communication with the working fluid supply path 108 to return working fluid from the supply path 108 to the heat exchange system 112.

The catheter 106 also has a distal heat exchange region 114 in accordance with present principles, which may be positioned into a patient such as the patient 120. The region 114 includes a generally linear path 116 and a helical return path 118 in fluid communication with each other. As shown in FIG. 7, the helical path 118 is understood to be generally helical, and may be a cylindrical or conical helix in accordance with present principles.

Also in accordance with present principles, the linear path 116 is understood to define at least a portion of the distal region 114 and is in and/or defines at least a portion of the supply path 108 in the exemplary embodiment shown. Also in exemplary embodiments such as the one shown in FIG. 7, the helical path 118 is understood to define at least a portion of the distal region 114 and is in and/or defines at least a portion of the return path 110. As may be appreciated from FIG. 7, the paths 116 and 118 do not overlap each other. The supply path is parallel to the axis of the helical return path but is not coaxial with it.

Figure 8:
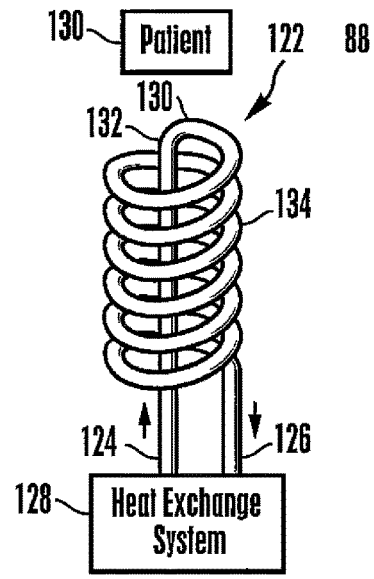
FIG. 8 shows another embodiment of the catheter with a straight supply tube that is parallel to and coaxial with the axis of a helical return tube, to ensure the coldest coolant is rapidly delivered to the distal-most portion of the catheter.

Now in reference to FIG. 8, a schematic diagram of a linear working fluid supply path that overlaps a generally helical working fluid return path is shown. Note that the generally linear working fluid supply path as described in reference to FIG. 8 is not to be confused with a generally linear body extending through a catheter, as described above. Thus, a catheter 122 has a working fluid supply path 124 communicating with a source of working fluid in accordance with present principles, such as the heat exchange system 128 shown in FIG. 8. The catheter 122 also has a working fluid return path 126 in fluid communication with the working fluid supply path 124 to return working fluid from the supply path 124 to the heat exchange system 128.

The catheter 122 also has a distal heat exchange region 130 in accordance with present principles, which may be positioned into a patient such as the patient 136. The region 130 includes a generally linear path 132 extending generally centrally through a helical return path 134, the paths 132 and 134 being in fluid communication with each other. As shown in FIG. 8, the helical path 134 is understood to be generally helical, and may be a cylindrical or conical helix in accordance with present principles.

Also in accordance with present principles, the generally linear path 132 is in and/or defines at least a portion of the supply path 124 in the exemplary embodiment shown. Also in exemplary embodiments such as the one shown in FIG. 8, the helical path 134 is in and/or defines at least a portion of the return path 126. As may be appreciated from the exemplary embodiment shown in FIG. 8, the paths 132 and 134 overlap each other such that the generally linear path 132 extends through the helical path 134. The supply path is both parallel to the axis of the helical return path and coaxial with it.

It may now be appreciated from FIGS. 2-8 that the alternate embodiments described above provide more surface area on the distal end of a catheter to contact a patient's blood when disposed in, e.g., a patient's vein to cool the blood of the patient. It is to be further understood that the embodiments described herein may also provide better blood mixing as blood contacts and passes by the distal end of the catheter. Thus, a patient's blood flow may change its path in, e.g., a vein as it contacts the increased surface area of the catheter, thereby promoting mixing of the blood and increasing heat transfer efficiency.

While the particular PATIENT TEMPERATURE CONTROL CATHETER WITH HELICAL HEAT EXCHANGE PATHS is herein shown and described in detail, it is to be understood that the subject matter which is encompassed by the present invention is limited only by the claims.

What is claimed is:

1. A catheter, comprising:
a working fluid supply path configured for communicating with a source of working fluid;
a working fluid return path configured for communicating with the working fluid supply path to return working fluid from the supply path to the source of working fluid; and
at least one of the paths being located at a distal heat exchange region of the catheter, the distal heat exchange region including at least a first helical path defining plural complete helical turns and configured for supplying working fluid to a distal portion of the catheter and at least a second helical path defining plural complete helical turns and configured for conveying working fluid away from the distal portion of the catheter, the first and second helical paths not being symmetrical to each other over all of the complete helical turns, at least respective first segments of the first and second helical paths not being axially distanced from each other.

2. The catheter of claim 1, wherein the distal heat exchange region is made of a shape memory material.

3. The catheter of claim 1, wherein the first helical path is in the working fluid supply path.

4. A method, comprising:
providing a working fluid supply path in a catheter and that is adapted to communicate with a source of working fluid; and
providing a working fluid return path in the catheter and that is adapted to communicate with the working fluid supply path to return working fluid from the supply path to the source of working fluid;
wherein at least one of the paths is located at a distal heat exchange region of the catheter, the distal heat exchange region including at least a first helical path defining plural complete helical turns and configured for supplying working fluid to a distal portion of the catheter and at least a second helical path defining plural complete helical turns and configured for conveying working fluid away from the distal portion of the catheter, the first and second helical paths not being symmetrical to each other over at least one pair of the respective complete helical turns.

5. The method of claim 4, wherein the distal heat exchange region is made of a shape memory material.

6. A catheter, comprising:
a working fluid supply path configured for communicating with a source of working fluid;
a working fluid return path configured for communicating with the working fluid supply path to return working fluid from the supply path to the source of working fluid;
wherein at least one of the paths is contained in a heat exchange region of the catheter, the heat exchange region including at least a first helical path configured for supplying working fluid to a distal end of the catheter and at least a second helical path configured for conveying working fluid away from the distal end of the catheter, the first and second helical paths not being symmetrical to each other over at least one pair of respective complete helical turns in the first and second helical paths, the first and second helical paths having the same number of turns as each other.

7. The catheter of claim 6, wherein the first helical path is cylindrical.

8. The catheter of claim 6, wherein the first helical path is conical.

* * * * *